United States Patent [19]

Maslanka

[11] Patent Number: 4,503,855
[45] Date of Patent: Mar. 12, 1985

[54] HIGH FREQUENCY SURGICAL SNARE ELECTRODE

[76] Inventor: Harald Maslanka, Stockacher Strasse 172, D-7200 Tuttlingen, Fed. Rep. of Germany

[21] Appl. No.: 454,689

[22] Filed: Dec. 30, 1982

[30] Foreign Application Priority Data

Dec. 31, 1981 [DE] Fed. Rep. of Germany ....... 3152019
Dec. 23, 1982 [DE] Fed. Rep. of Germany ....... 3247793

[51] Int. Cl.³ .............................................. A61B 17/39
[52] U.S. Cl. ................................................ 128/303.15
[58] Field of Search ...................... 128/303.14, 303.15, 128/303.16, 303.17, 784-786

[56] References Cited

U.S. PATENT DOCUMENTS

| | | | |
|---|---|---|---|
| 3,149,633 | 6/1961 | Zingale | 128/303.15 |
| 3,910,279 | 10/1975 | Okada et al. | 128/303.15 |
| 4,181,131 | 1/1980 | Ogiu | 128/303.15 |

FOREIGN PATENT DOCUMENTS

| | | | |
|---|---|---|---|
| 2132808 | 1/1973 | Fed. Rep. of Germany | 128/303.14 |
| 2514501 | 10/1976 | Fed. Rep. of Germany | 128/303.17 |
| 2941060 | 4/1980 | Fed. Rep. of Germany | 128/303.14 |
| 2275226 | 1/1976 | France | 128/303.17 |

*Primary Examiner*—Lee S. Cohen
*Attorney, Agent, or Firm*—Wood, Dalton, Phillips, Mason & Rowe

[57] ABSTRACT

The diathermy electrode comprises a flexible insulating guide tube (1) in which a flexible electrode lead (3) adapted to be connected to a diathermy current source is slidably displaceably disposed. Attached to the free end of the electrode lead (3) next to the patient is a resilient electrode snare (5) which is capable of resiliently spreading apart when slidably moved out of the guide tube (1) and which is adapted to be completely retractable into the guide tube (1) by the electrode lead (3). The end of the electrode snare (5) facing away from the electrode lead (3) is provided with a metal head (21) which prevents the snare from burning through. The snare halves (7, 9) enter the metal head (21) from the same side and form a wedge type cutter (25). The forward face (27) of the guide tube (1) is slanted to form an angle of 30° to 60° with the tube axis. The metal head (21) is coated with an insulating layer (23) to prevent unintentional damage to the tissue, particularly perforations of the intestine during the removal of intestinal polyps.

11 Claims, 3 Drawing Figures

HIGH FREQUENCY SURGICAL SNARE ELECTRODE

BACKGROUND OF THE INVENTION

This invention relates to a high frequency surgical snare electrode, particularly for endoscopes having an instrument channel for slidably displaceably receiving the electrode, a flexible guide channel insulated at least on the outside, a flexible electrode lead slidably displaceable in the guide channel, and a resilient snare electrode attached to the free end of the electrode lead next to the patient and being capable of resiliently spreading apart when moved out of the guide channel and of being completely or nearly completely retracted into the guide channel by the electrode lead.

High frequency surgical snare electrodes of the foregoing type are known from the German published patent specification (Auslegeschrift) No. 21 32 808 or the German published patent application (Offenlegungsschrift) No. 29 41 060. The snare electrode is used in the removal of growths, such as stomach and intestinal polyps, for example, whereby the growth formations are excised by electrotomy, implemented by retracting the snare electrode connected by the electrode lead to a source of power.

The known snare electrode is provided at its end opposite the electrode lead with a semi-circularly curved section, the diameter of which is smaller than a guide bushing positioned at the confronting end of the guide channel, and smaller than the inner diameter of the guide channel. The semi-circular curvature is intended to ensure that the elasticity limit of the snare wire is not exceeded when the snare electrode is completely retracted.

The diameter of the wire of the snare electrode is very small in order to keep the diameter of the guide channel as small as possible. The known snare electrodes are exposed to strong thermal forces exerted by the cutting current on the area of the curved section and tend to burn through at a point along the curvature already after short use.

SUMMARY OF THE INVENTION

It is a first object of the invention to improve a snare electrode of the known type so that it will no longer, or not as easily as before, burn through at its end remote from the electrode lead.

This is achieved according to the invention, in that the end portion of the snare electrode opposite the electrode lead is provided with a metal head. The metal head constitutes a cooling body due to which the heat capacity of that area of the electrode snare is increased which is subjected to strong thermal stresses so that it is made much more difficult or even impossible for the electrode to burn through.

In a preferred embodiment, the ends of the snare halves opposite the electrode lead are approaching from the same side and, being laid parallel adjacent each other, are securely joined to each other. These fixedly joined end sections are not used for cutting but, rather, they form the cooling body which is positioned adjacent the cutting area of the union of the two halves of the snare. For improved thermal conductivity, the two snare or loop halves may be soldered together; a mechanically stable connection may, however, also be achieved by the application of an adhesive.

A construction of the foregoing type has additional mechanical advantages over conventional snare electrodes. In the known prior snare electrode, the growth formation snared in the loop tends to spread the end sections of the loop halves joined by a semi-circular curved section apart in an area where the mechanical strength already is diminished due to the bending. Thus, the semi-circularly curved section of the prior snare electrode is frequently deformed when the growth is cut off; this deformation is neutralized or compensated for by another deformation occurring during the retraction of the snare electrode into the guide channel, if the diameter of the curvature is larger than the inner diameter of the guide channel. In the construction proposed by the present invention, the end sections of the snare halves extend parallel to each other, with no sharp angular break, whereby the mechanical strength is substantially increased, on the one hand, and the cutting capacity of the snare is enhanced, on the other hand. The snare halves form a kind of wedge cutter into which the growth formation to be removed is thrust as the snare electrode is retracted into the guide channel. The tensional forces required for excising the growth may thus be substantially reduced.

In a preferred embodiment, the end sections pass from the same side into a sleeve or cap. The sleeve or cap increases the mechanical stability of the junction of the end sections of the snare halves. The sleeve or cap may be made of metal to increase the cooling capacity.

The sleeve or cap may, however, also be made of an electrically insulating material. This type of construction serves to prevent the destruction of body tissue due to unintentional contact with the current carrying tip of the snare electrode. Particularly in the removal of intestinal polyps, there is danger of perforating the wall of the intestine with the point of the snare electrode. This type of injury cannot occur with this particular construction. The same result may be achieved with a metallic sleeve or cap whose surface facing away from the electrode lead is coated with an electrically insulating material.

The idea of preventing unintentional tissue destruction may be applied also to other high frequency surgical snare electrodes. It is therefore another object of the present invention to improve a prior snare electrode in a manner such that unintentional tissue destruction by the end section of the snare electrode remote of the electrode lead is avoided.

This second object is accomplished according to the invention in that the end section of the snare electrode opposite the electrode lead in its retracted state is provided with an insulating member to protect the snare electrode from making electrical contact in this area. For this purpose, a prior art snare electrode may have at least the surface of the semi-circular curvature disposed at the outer side of the tip of the snare electrode coated with an insulating material. Preferably, the insulating member is in the form of a sleeve or cap for receiving the end sections of the snare halves remote from the electrode lead which, in particular, are coming from the same side. The sleeve or cap may be made completely of an insulating material, or it may have a metal core coated at least in part with an insulating material. Sleeves or caps consisting completely of an insulating material simplify the manufacturing process. In sleeves or caps having a metal core, the tip of the snare electrode subjected to strong thermal action during the excision procedure is cooled and will no longer, or not as easily, burn through.

Another feature of the present invention facilitates the removal of the growth formation by retracting the electrode snare into the electrode channel. To this end, the terminal section of the guide channel proximal to the snare electrode is provided with a front face inclined at an angle of less than 90° with respect to the channel axis. The front face of the guide channel forming an angle with the channel axis of preferably 30° to 60° has a plurality of functions. First, it facilitates the excision of the growth. Secondly, it assists in the insertion of the metal head or the insulating member, respectively, into the guide channel. Finally, the oblique forward face of the guide channel stabilizes the angular position of the snare electrode outside the guide channel since the end sections of the resiliently diverging snare halves facing the electrode lead have a tendency to adjust the plane of the snare transversely to the fall line of the oblique forward face.

All of the embodiments described in the foregoing are not only suitable for snare electrodes which are symmetrical about the channel axis, but both the features of adding a cooling body and of providing an insulating member may be utilized also in unsymmetrical snare electrodes as, for example, in snare electrodes in which merely one snare half is fixedly connected to the electrode lead, while the end section of the other snare half facing the electrode lead is slidably displaceably attached to the fixed snare half or the electrode lead. In a snare electrode of this type, a stop provided at the end of the guide channel prevents the slidably displaceable end of the second snare half from being pushed out of the guide channel. Thus, the snare is deformed unsymmetrically as the electrode lead is slidably moved out. The metal head, or the insulating member, respectively, is positioned at that point of the unsymmetrical snare which forms the snare end next to the patient when the snare is completely or nearly completely retracted into the guide channel.

BRIEF DESCRIPTION OF THE DRAWING

In the following, embodiments of the invention will be described in further detail with reference to the drawings, in which.

DESCRIPTION OF THE PREFERRED EMBODIMENTS

Figure 1:
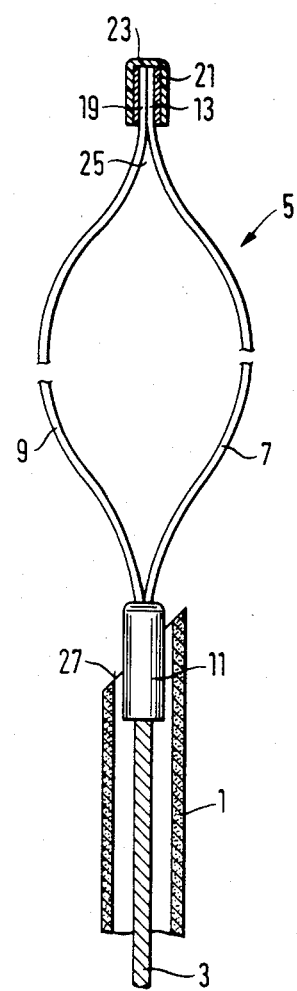
FIG. 1 is a partially sectional view of the end section of a snare electrode next to the patient.

The high frequency surgical snare electrode of FIG. 1 is provided with a flexible and insulating guide channel or tube 1 made of polytetrafluoroethylene, for example, in which an electrode lead 3 made of flexible stranded wire is slidably displaceably disposed. Attached to the end of the electrode lead 3 which is proximal to the patient is a snare electrode 5 which is symmetrical about the channel axis. The resilient snare halves 7, 9 are made of stranded wire and are secured on one end to the electrode 3 by means of a metal bushing 11. The end portions 13, 19 of the snare halves 7, 9 opposite the metal bushing 11 are positioned parallel adjacent each other and are passed through a metal sleeve 21 to which they are joined by soldering, for example, and with which they maintain good thermal contact. The surfaces of the metal sleeve 21 facing away from the electrode lead 3, particularly its outer circumferential shell and the forward face directed away from the electrode lead 3 are coated with an insulating layer 23.

The resilient snare halves 7, 9 of the snare electrode 5 are of a configuration such as to be able to automatically spread apart outside of the guide channel 1. The diameter of the metal sleeve 21 including the insulating layer 23, the diameters of the snare halves 7, 9 and the diameter of the metal bushing 11 are so dimensioned that the snare electrode 5 is capable of being completely retracted into the guide channel 1. As the electrode is retracted, the loop closes, cutting off the growth caught in the snare. The cut is coagulated by the current supplied at the end of the electrode lead 3 remote from the snare.

The end sections of the snare halves 7, 9 opposite the electrode lead 3 enter the metal sleeve 21 from the same side and form a wedge cutter 25 which is capable of excising the growth formation without requiring any substantial tensional forces. To improve the cutting action, the tubular guide channel or hose 1 is additionally provided with a forward face 27 inclined to its axis. The angle that the front face 27 forms with the hose axis is about 45°. The oblique forward face furthermore facilitates the withdrawal of the metal sleeve 21 and stabilizes the angular position of the plane of the loop transversely to the fall line of the forward face 27 extending in the plane of the drawing. The loop plane, for the sake of clarity shown in the drawing to be in the plane of the drawing, thus extends perpendicular to the plane of the drawing. Alternatively, however, the the forward face 27 may also extend perpendicular to the hose axis.

The insulating layer 23 prevents injury to body tissue resulting from an unintentional contact of the tissue with the electrode snare 5 which carries a high frequency voltage. Such injury may take the form of perforation of the intestine during removal of intestinal polyps, for example. However, the insulating layer 23 may also be omitted.

Figure 2:
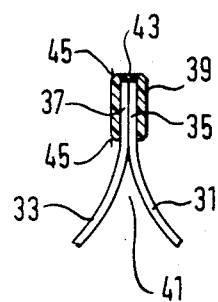
FIGS. 2 and 3 are partially sectional views of the area of union of snare halves of different embodiments of the snare electrode.

FIG. 2 illustrates a different embodiment of the end section of a snare electrode proximal to the patient, forming two loop halves 31, 33. The end sections 35, 37 next to the patient extend parallel closely adjacent each other and pass through an insulating sleeve 39 made of a plastic or ceramic material or the like. The end sections 35, 37 are secured inside the insulating sleeve 39 by means of an adhesive and may additionally be soldered to each other. The end sections 35, 37 constitute a cooling body for the cutting area 41 of the snare electrode 5 forming a kind of a wedge cutter at the end of the insulating sleeve remote from the patient. The cooling body enhances the thermal capacity of the cutting area. The insulating sleeve imparts sufficient mechanical strength to the area of union and prevents any unintentional destruction of tissue by the end sections 35, 37. The forward faces of the end sections 35, 37 next to the patient are slightly recessed in the insulating sleeve 39 to avoid any contact, and are coated with an insulating material 43 such as, for example, the adhesive used for securing the end sections 35, 37 inside the insulating sleeve 39. The edges of the rim of the insulating sleeve 38 are bevelled or rounded, as it is indicated at 45.

Figure 3:
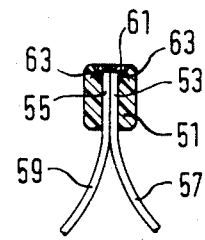

FIG. 3 shows another embodiment of a thermically stable and tissue destruction preventive tip of a high frequency surgical snare electrode. It is distinguished from the electrode tip of FIG. 2 merely by the two end sections 53 and 55 of the two snare halves 57 and 59, which are inserted into an insulating sleeve 51 made of a plastic or ceramic material and, in particular, are secured therein by an adhesive. The two end sections 53 and 55 are provided in the area proximal to the patient with a glob of solder 61 or the like which fits into an undercut 63 at the front face of the insulating sleeve 53 next to the patient. The solder glob 61 renders it more difficult for the snare halves 57, 59 to be pulled out of the insulating sleeve 53. For a discussion of the function and mode of operation of the embodiment of FIG. 3 reference is made to the description of the embodiment of FIG. 2. The embodiments of FIGS. 2 and 3 are preferred for use with a snare electrode otherwise corresponding to FIG. 1. The connecting members in the form of cooling bodies and protective insulation provided at the ends of the snare halves next to the patient, as shown in FIGS. 1 to 3, may also be used in conjunction with unsymmetrical high frequency surgical snare electrodes.

I claim:

1. An improved high frequency surgical snare electrode instrument, particularly for endoscopes, of the type having a guide channel (1) with an outer peripheral surface that is at least externally insulated, an electrode lead (3) slidably displaceable in the guide channel, and a resilient snare electrode (5) attached to a free end of the electrode lead, capable of resiliently spreading apart when moved out of the guide channel and at least partially retractable into the guide channel by the electrode lead, said resilient snare electrode having first and second halves cooperatively defining a cutting loop portion used to surround a growth which is to be excised, the improvement comprising:
   said first and second snare electrode halves extending away from said cutting loop portion to define a cooling extension, said first and second halves engaged intimately along said cooling extension; and
   means maintaining said first and second halves intimately engaged along said cooling extension,
   said cooling extension being movable relative to said guide channel upon slidably displacing said electrode lead within said channel;
   said cooling extension increasing the heat capacity of said snare electrode, particularly at the cutting loop portion, to prevent failure of the snare occasioned by thermal stress.

2. The improved high frequency surgical snare electrode according to claim 1 wherein said means comprises a metal head surrounding the first and second halves along the cooling extension.

3. The improved high frequency surgical snare electrode according to claim 1 wherein said first and second snare electrode halves each have a first end connected to the electrode lead and a second end remote from the electrode lead and the first and second snare electrode halves are in parallel, intimate engagement along said cooling extension adjacent the second ends of the snare electrode halves.

4. The improved high frequency surgical snare electrode according to claim 3 characterized in that the second ends (13, 19; 35, 37; 53, 55) of the snare electrode halves (7, 9; 31, 33; 57, 59) extend without angular break within or adjacent the area where they are fixedly joined to each other.

5. The improved high frequency surgical snare electrode according to claim 1 wherein said means comprise a sleeve surrounding said first and second halves.

6. The improved high frequency surgical snare electrode according to claim 5, characterized in that the sleeve (21) is made of metal.

7. The improved high frequency surgical snare electrode according to claim 6, characterized in that the sleeve (21) is coated with an electrically insulating layer (23) on the surface facing away from the electrode lead (3).

8. The improved high frequency surgical snare electrode according to claim 5, characterized in that the sleeve (39; 51) is made of an electrically insulating material.

9. The improved high frequency surgical snare electrode according to claim 1, characterized in that a terminal section of the guide channel (1) adjacent the snare electrode (5) is provided with a forward face inclined at an angle of less than 90° with respect to the channel axis.

10. The improved high frequency surgical snare electrode according to claim 9, characterized in that the angle formed by the forward face (27) with the channel axis is between 30° and 60°.

11. An improved unipolar high frequency surgical snare electrode instrument, particularly for endoscopes, of the type having a guide channel (1) with an outer peripheral surface that is at least externally insulated, an electrode lead (3) slidably displaceable in the guide channel, and a resilient snare electrode (5) attached to a free end of the electrode lead, capable of resiliently spreading apart when moved out of the guide channel and retractable into the guide channel by the electrode lead, said resilient snare electrode having first and second halves cooperatively defining a cutting loop portion used to surround a growth which is to be excised, the improvement comprising:
   the end portions of the first and second snare electrode halves remote from the electrode lead are in extended intimate surface engagement,
   and an insulating member on said end portions of the first and second snare electrode halves,
   said insulating member retractable into the channel and protecting the snare electrode from making electrical contact with body tissue in the vicinity of where the high frequency surgical snare electrode is used.

* * * * *